US011393178B2

(12) United States Patent
Shirazian et al.

(10) Patent No.: US 11,393,178 B2
(45) Date of Patent: Jul. 19, 2022

(54) MULTI-MODAL VISUALIZATION IN COMPUTER-ASSISTED TELE-OPERATED SURGERY

(71) Applicant: INTUITIVE SURGICAL OPERATIONS, INC., Sunnyvale, CA (US)

(72) Inventors: Pourya Shirazian, Sunnyvale, CA (US); Mahdi Azizian, Sunnyvale, CA (US); Daniel Proksch, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 17/266,304

(22) PCT Filed: Jul. 31, 2019

(86) PCT No.: PCT/US2019/044441
§ 371 (c)(1),
(2) Date: Feb. 5, 2021

(87) PCT Pub. No.: WO2020/033208
PCT Pub. Date: Feb. 13, 2020

(65) Prior Publication Data
US 2021/0304512 A1    Sep. 30, 2021

Related U.S. Application Data

(60) Provisional application No. 62/715,407, filed on Aug. 7, 2018.

(51) Int. Cl.
*G06T 17/20* (2006.01)
*G06T 19/00* (2011.01)
(Continued)

(52) U.S. Cl.
CPC .......... *G06T 19/006* (2013.01); *A61B 90/37* (2016.02); *G06T 17/20* (2013.01); *G06T 19/20* (2013.01);
(Continued)

(58) Field of Classification Search
CPC ....... G06T 19/006; G06T 17/20; G06T 19/20; G06T 2210/41; A61B 90/37; A61B 2090/3762
See application file for complete search history.

(56) References Cited

U.S. PATENT DOCUMENTS 9,503,681 B1 * 11/2016 Popescu ............... G06F 40/169
10,021,351 B2 * 7/2018 Jessop ..................... A61B 1/04
(Continued)

OTHER PUBLICATIONS

International Preliminary Report on Patentability for Application No. PCT/US2019/044441, dated Feb. 18, 2021, 14 pages.
(Continued)

*Primary Examiner* — Said Broome
(74) *Attorney, Agent, or Firm* — Fish & Richardson P.C.

(57) ABSTRACT

Technology described herein can be embodied in a method of providing visual feedback during surgery. The method includes obtaining a set of vectors representing a model of an anatomical organ, the set produced from a representation of the organ as imaged under one or more imaging modalities. The method includes obtaining a set of pixel positions of a display device, wherein the pixel positions correspond to a view of the organ. The method further includes generating, using at least a portion of the set of vectors, multiple fragment-vectors for each pixel position in the set of pixel positions, the multiple fragment-vectors each representing a corresponding portion of the organ along a line-of-sight through the organ, and generating a pixel value for each pixel position in the set of pixel positions, and presenting, on
(Continued)

the display device, an augmented image of the view of the organ using the generated pixel values.

20 Claims, 8 Drawing Sheets

(51) Int. Cl.
 *A61B 90/00* (2016.01)
 *G06T 19/20* (2011.01)
(52) U.S. Cl.
 CPC . *A61B 2090/374* (2016.02); *A61B 2090/3762* (2016.02); *G06T 2200/24* (2013.01); *G06T 2210/41* (2013.01); *G06T 2210/62* (2013.01); *G06T 2219/2012* (2013.01)

(56) References Cited

U.S. PATENT DOCUMENTS

| | | | | |
|---|---|---|---|---|
| 10,071,306 | B2* | 9/2018 | Vandonkelaar | A63F 13/25 |
| 10,398,514 | B2* | 9/2019 | Ryan | A61B 90/37 |
| 10,687,901 | B2* | 6/2020 | Thomas | G06T 19/20 |
| 2006/0052661 | A1* | 3/2006 | Gannot | A61B 18/24 |
| | | | | 600/108 |
| 2008/0140056 | A1* | 6/2008 | Keimel | A61M 25/0102 |
| | | | | 604/891.1 |
| 2008/0253525 | A1* | 10/2008 | Boyden | G01V 5/0008 |
| | | | | 378/87 |

OTHER PUBLICATIONS

Cruz A. LA., et al., "Medical Image Rendering and Description Driven by Semantic Annotations," International Conference on Financial Cryptography Data Security; [lecture Notes in Computer Science; Leet. Notes Computer], May 2012, pp. 123-149.
International Search Report and Written Opinion for Application No. PCT/US2019/044441, dated Jan. 24, 2020, 21 pages.
Liu W.P. et al., "Augmented Reality and Cone Beam CT Guidance for Transoral Robotic Surgery," Journal of Robotic Surgery, Sep. 2015, vol. 9 (3), pp. 223-233.
Shahidi R., et al., "Volumetric Image Guidance via a Stereotactic Endoscope," Medical Image Computing and Computer-Assisted Intervention (MICCAI). International Conference. Proceedings, Oct. 1998, pp. 241-252.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

MULTI-MODAL VISUALIZATION IN COMPUTER-ASSISTED TELE-OPERATED SURGERY

CLAIM OF PRIORITY

This application is a U.S. National Stage Application under U.S.C. § 371 and claims the benefit of International Patent Application No. PCT/US2019/044441, filed on Jul. 31, 2019, which claims the benefit of priority to U.S. Provisional Application 62/715,407, filed on Aug. 7, 2018, the entire contents of both of which are incorporated herein by reference.

TECHNICAL FIELD

This disclosure relates to devices and methods for minimally invasive computer-assisted tele-operated surgery.

BACKGROUND

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. The surgeon performs the surgical procedures on the patient by manipulating master control input devices, which in turn control the motion of robotic instruments.

SUMMARY

In one aspect, this document features a method of providing visual feedback during a surgical process on a display device. The method includes obtaining a set of vectors representing a model of an anatomical organ, wherein the set of vectors is produced from a representation of the organ as imaged under one or more imaging modalities. The method also includes obtaining a set of pixel positions of a display device, wherein the pixel positions correspond to a view of the organ. The method further includes generating, using at least a portion of the set of vectors, multiple fragment-vectors for each pixel position in the set of pixel positions, the multiple fragment-vectors each representing a corresponding portion of the organ along a line-of-sight through the organ. Each fragment-vector includes a depth value of a location of the corresponding portion associated with the fragment, the depth value representing a distance of the location from a reference point, a color value associated with the corresponding portion, an identifier of a different fragment vector corresponding to an adjacent portion, and an identifier of a tissue type corresponding to the tissue portion associated with the fragment. The method also includes generating a pixel value for each pixel position in the set of pixel positions, wherein the pixel value is generated based on the color values and depth values associated with the corresponding fragment-vectors, and presenting, on the display device, an augmented image of the view of the organ using the generated pixel values.

In another aspect, this document features a surgical system that includes a display device, and a shading engine that includes one or more processing devices. The shading engine is configured to obtain a set of vectors representing a model of an anatomical organ, wherein the set of vectors is produced from a representation of the organ as imaged under one or more imaging modalities. The shading engine is also configured to obtain a set of pixel positions of a display device, wherein the pixel positions correspond to a view of the organ. The shading engine is further configured to generate, using at least a portion of the set of vectors, multiple fragment-vectors for each pixel position in the set of pixel positions, the multiple fragment-vectors each representing a corresponding portion of the organ along a line-of-sight through the organ. Each fragment-vector includes a depth value of a location of the corresponding portion associated with the fragment, the depth value representing a distance of the location from a reference point, a color value associated with the corresponding portion, an identifier of a different fragment vector corresponding to an adjacent portion, and an identifier of a tissue type corresponding to the tissue portion associated with the fragment. The shading engine is further configured to generate a pixel value for each pixel position in the set of pixel positions, wherein the pixel value is generated based on the color values and depth values associated with the corresponding fragment-vectors, and present, on the display device, an augmented image of the view of the organ using the generated pixel values.

In another aspect, this document features one or more machine-readable non-transitory storage devices encoded with machine-readable instructions configured to cause one or more processing devices to perform various operations. The operations include obtaining a set of vectors representing a model of an anatomical organ, wherein the set of vectors is produced from a representation of the organ as imaged under one or more imaging modalities. The operations also include obtaining a set of pixel positions of a display device, the pixel positions corresponding to a view of the organ, and generating, using at least a portion of the set of vectors, multiple fragment-vectors for each pixel position in the set of pixel positions, the multiple fragment-vectors each representing a corresponding portion of the organ along a line-of-sight through the organ. Each fragment-vector includes a depth value of a location of the corresponding portion associated with the fragment, the depth value representing a distance of the location from a reference point, a color value associated with the corresponding portion, an identifier of a different fragment vector corresponding to an adjacent portion, and an identifier of a tissue type corresponding to the tissue portion associated with the fragment. The operations also include generating a pixel value for each pixel position in the set of pixel positions, wherein the pixel value is generated based on the color values and depth values associated with the corresponding fragment-vectors, and presenting, on the display device, an augmented image of the view of the organ using the generated pixel values.

Implementations of the above aspects can include one or more of the following features, The one or more imaging modalities can include at least one of: computerized tomography (CT), ultrasound imaging, positron emission tomography-CT (PET-CT), a single-photon emission CT (SPECT), magnetic resonance imaging (MRI), and a cone-beam CT (CBCT). The set of vectors can include multiple sub-vectors each representing a triangle mesh representing a particular type of anatomical structure in the organ. Each of the multiple sub-vectors can include a list of vertices and triangles associated with the corresponding triangle mesh. Generating the pixel value can include sorting the corresponding fragment-vectors based on the associated depth values, assigning a transparency factor to each of the color values associated with the corresponding fragment vectors, and generating the pixel value as a weighted combination of the color values weighted by the corresponding transparency factors. The transparency factors can be assigned based on a user input indicative of a depth of visualization. The transparency factors can be assigned based on a user input indicative of a type of tissue to be displayed on the augmented image. Responsive to presenting the augmented image, user input including one or more markers identifying particular portions on the organ can be received, and the one or more markers can be presented overlaid on the augmented image. The locations of the one or more markers in the augmented image is updated with changes to the locations of the particular portions in the view of the organ. Responsive to presenting the augmented image, user input identifying two discrete portions on the organ can be received, a distance between the two portions can be computed based at least on information in the fragment-vectors corresponding to the two discrete portions, and the computed distance can be presented overlaid on the augmented image. The distance between the two discrete portions can be computed as a distance along a surface of the organ on which the portions are located, or as a distance through the organ. A representation of a line connecting the two discrete portions along a surface of the organ on which the portions are located can be presented, overlaid on the augmented image. At least one of the two discrete portions can represent a boundary of an endophytic mass located at a depth under the surface of the organ. The multiple fragment vectors can be generated using a rasterization process on the portion of the set of vectors.

Some or all of the embodiments described herein may provide one or more of the following advantages. In some cases, an augmented three dimensional (3D) visualization of a surgical site can be provided by displaying a synthetic view overlaid on a live view of the surgical site. The synthetic view can be based on a rendering model that allows a surgeon to view portions of organs that are occluded in the live view by other portions or tissues closer to the surgeon in the line of sight. The synthetic view can be made interactive, thereby allowing the surgeon to switch between various types of visualizations (e.g., based on depth, tissue type etc.), as well as place virtual markers on the synthetic view, for example, to mark locations of tumors. In some cases, such virtual marking can allow the surgeon to avoid burning portions of the organ to demarcate the boundary of the tumor, which in turn contributes to making the surgery less invasive. By maintaining a registration of the synthetic view with the live view, and updating the synthetic view in accordance with changes to the live view, the technology described herein facilitates an improved augmented visualization for the surgeon, which in turn can potentially improve the overall surgical process, for example, by helping the surgeon better visualize the underlying vasculature and/or other adjoining tissue structures, without having to refer to other independent images. In some cases, the technology allows for measuring distances between portions of an organ, either along a surface, or through intervening tissues, thereby allowing the surgeon to better understand the environment in which the surgery is being performed.

DETAILED DESCRIPTION

Figure 2:
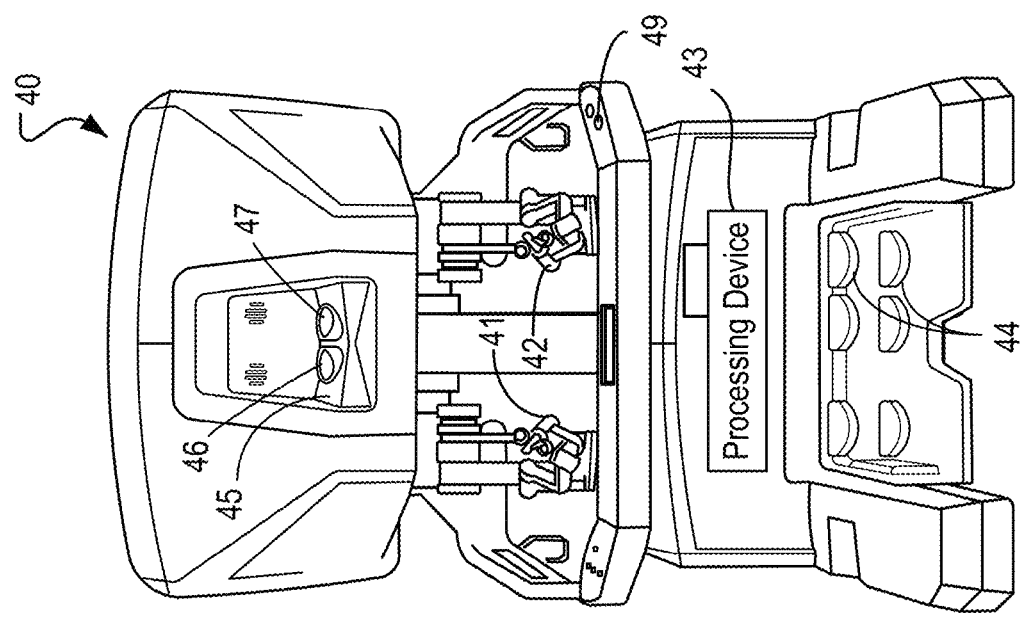
FIG. 2 is a front view of an example surgeon console of a computer-assisted tele-operated surgery system.

This document describes technology that, in some cases, improves visualization of surgical sites and anatomical parts during image-guided surgical processes such as minimally invasive robot-assisted surgery (also referred to herein as minimally invasive surgery (MIS)). For example, a synthetic view generated using a particular imaging modality (e.g., computerized tomography (CT), ultrasound imaging, positron emission tomography-CT (PET-CT), a single-photon emission CT (SPECT), magnetic resonance imaging (MRI), and a cone-beam CT (CBCT), etc.) can be rendered on a surgeon's console registered with a live view of a surgical scene. In some cases, such augmented rendering of the surgical scene allows the surgeon to view various types of information without taking his gaze or focus away from the surgical scene. For example, because the synthetic view can be configured to render/display information at various depths along a line of sight, the surgeon may be able to view portions of an organ or tissue that is occluded in the live view. In some cases, this can allow the surgeon to view vasculature, depth of endophytic mass, distribution of various types of tissues in the surgical scene etc., without having to obtain such information from independent sources such as a CT scan of the surgical scene displayed in a separate display device or in a separate portion of the same display device. In some implementations, the synthetic view can be displayed registered with respect to the live view from an endoscope, and adaptively updated in accordance with the changes in view of the live image. In some implementations, the synthetic view can be made interactive, which can allow the surgeon to measure distances between various portions of the surgical scene, have distance. information and/or rulers displayed on the augmented view, and/or put virtual markers on the surgical scene (e.g., to mark a boundary of a tumor). Overall, the technology described herein allows for an improved visualization of a surgical scene, which in turn may allow a surgeon to carry out a surgical process with increased efficiency and accuracy.

Aspects of the invention are described primarily in terms of an implementation using a da Vinci® Surgical System, commercialized by Intuitive Surgical, Inc. of Sunnyvale, Calif. Examples of such surgical systems are the da Vinci® Xi™ Surgical System (Model IS4000) and the da Vinci® Si™ HD™ Surgical System (Model IS3000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

Figure 1:
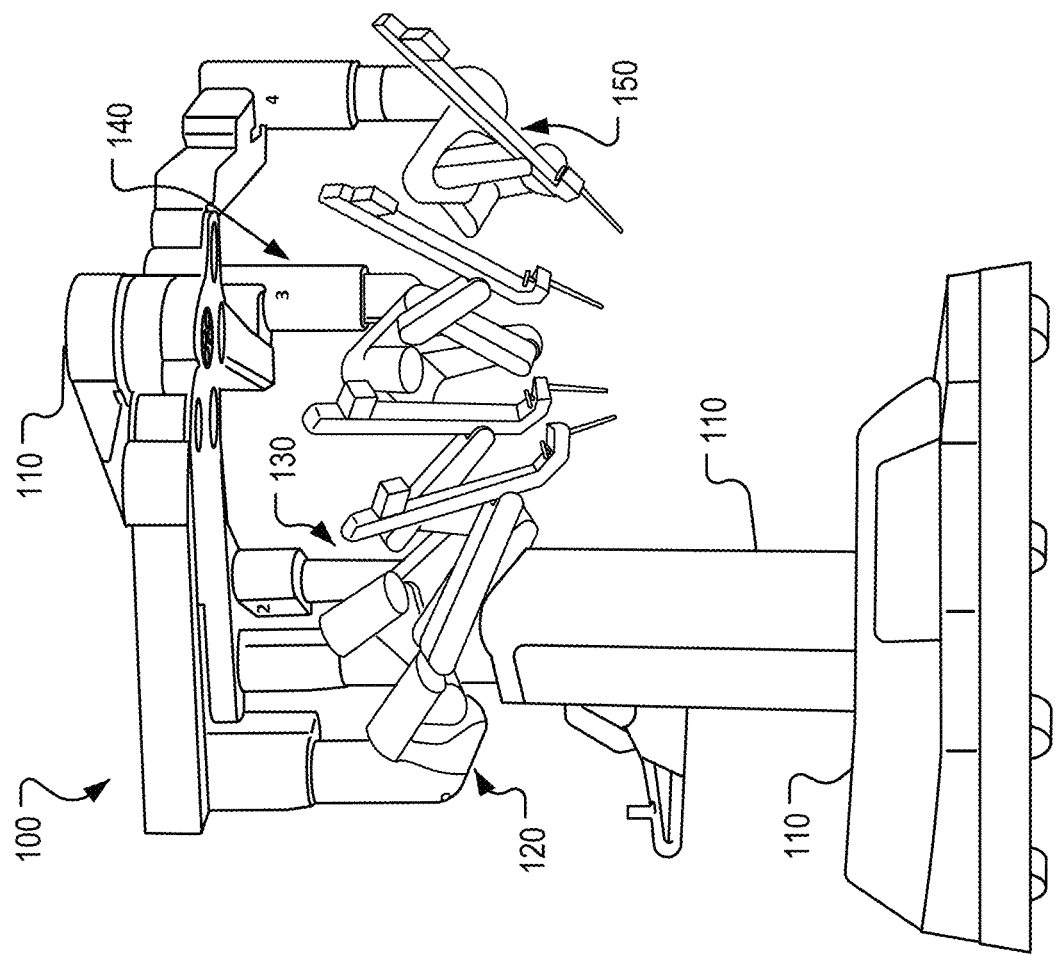
FIG. 1 is a perspective view of an example patient-side cart of a computer-assisted tele-operated surgery system.

Referring to FIGS. 1 and 2, systems for minimally invasive computer-assisted telesurgery (also referred to as MIS) can include a patient-side cart 100 and a surgeon console 40. Telesurgery is a general term for surgical systems where the surgeon uses some form of remote control, e.g., a servo-mechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment, the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 with toe and heel controls are provided on the surgeon console 40 so the user may control movement and/or actuation of devices associated with the foot pedals.

A processing device 43 is provided in the surgeon console 40 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), field-programmable gate arrays (FPGAs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processing device 43 may also be distributed as subunits throughout the telesurgery system. One or more of the subunits may be physically remote (e.g., located on a remote server) to the telesurgery system.

Figure 3:
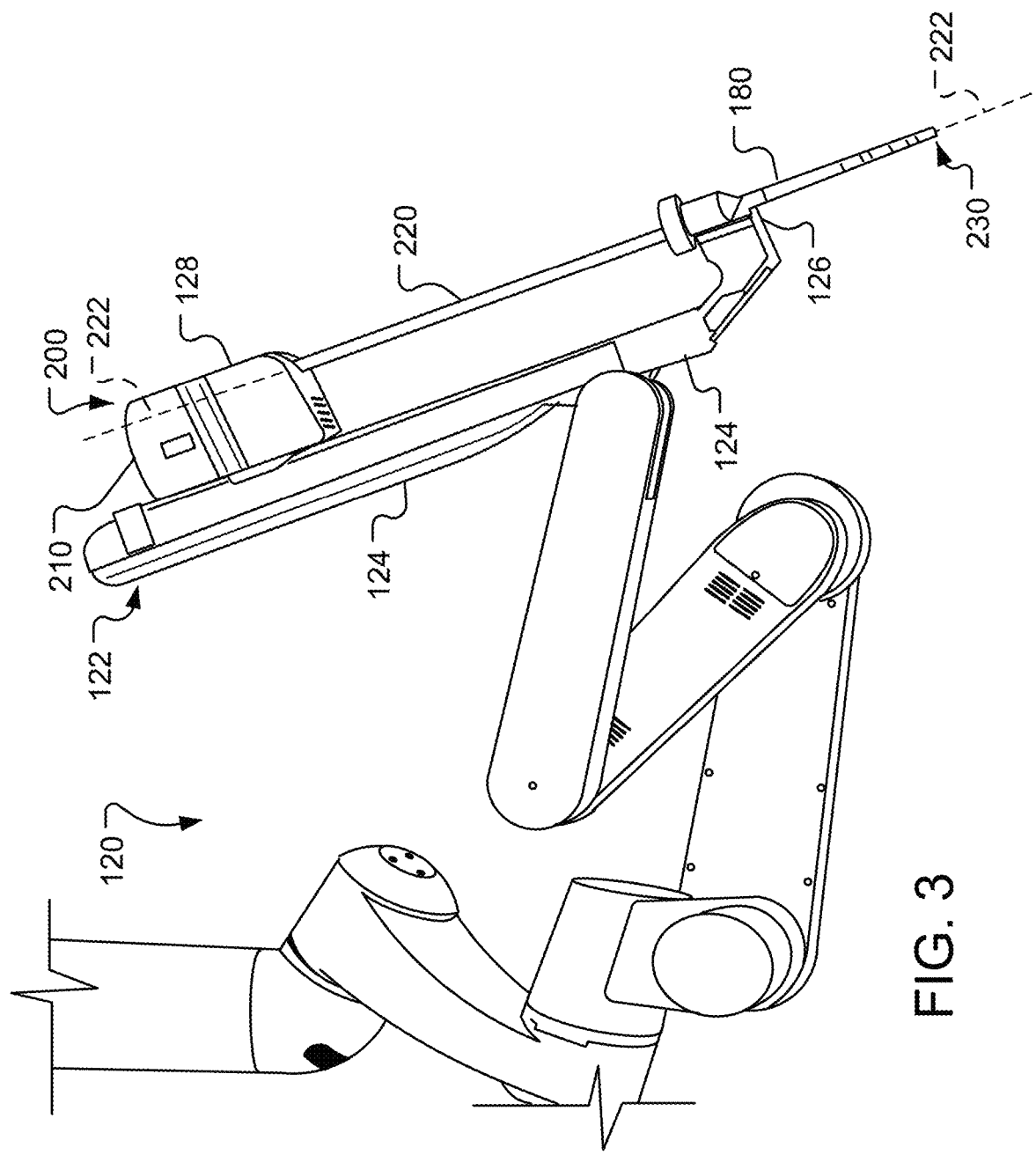
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform MIS. For example, in the depicted arrangement the robotic manipulator arm assembly 120 is pivotably coupled to an instrument holder 122. A cannula 180 and a surgical instrument 200 are, in turn, releasably coupled to the instrument holder 122. The cannula 180 is a hollow tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43. The surgical instrument 200 includes a transmission assembly 210, the elongate shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
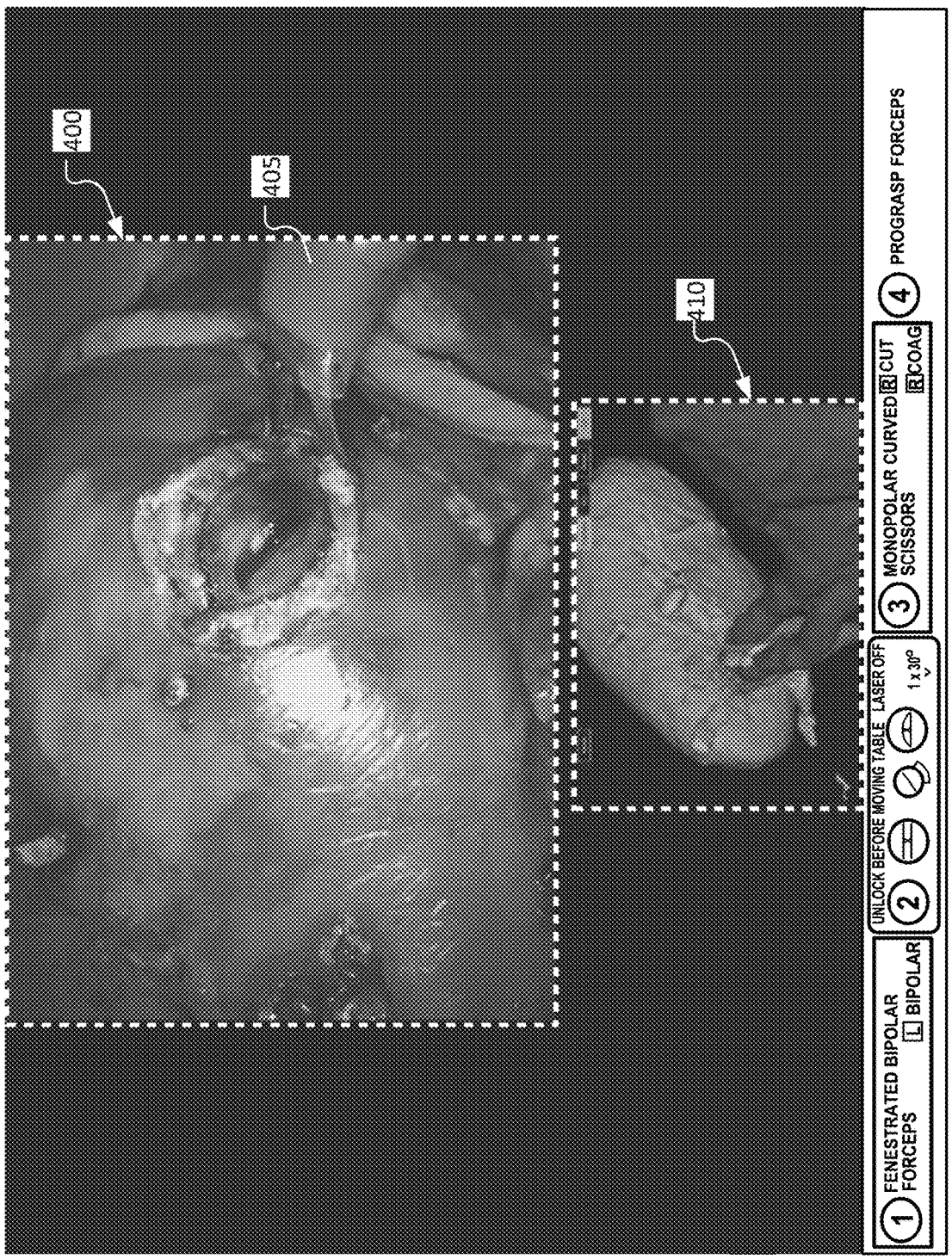
FIG. 4 shows an example of a view generated at the surgeon, wherein a live view is displayed separately from view of a different modality.

In some implementations, a robotic manipulator arm assembly 120 can be used to hold and manipulate a surgical tool at the surgical site. FIG. 4 shows an example of a corresponding view generated at the surgeon, wherein a live view 400 is displayed separately from view 410 of a different modality. In this example, the surgical tool 405 is being operated by a robotic manipulator arm assembly to perform a surgical process. The live view 400 presents the view captured by the endoscope, and does not provide information that is not directly visible in the endoscope images. For example, portions of vasculature, diseased tissues (e.g., tumors), or other tissues underlying the surface of the organ may not be visible in the live view. While such information may be made available through a separate view 410 of a different modality, the surgeon has to switch focus between the two images to get a sense of the overall surgical environment. This in turn can cause a significant amount of time to be spent on locating and marking diseased tissues in the organ. Further, when a diseased tissue is located, the surgeon may have to use physical markers or energy tools (e.g., to burn markers directly on the tissue) to demarcate the location of the diseased tissues. Such marking may not only be time-consuming, but also make the process additionally invasive, for example by affecting elasticity of the burned tissues.

The technology described herein facilitates augmenting the live view from an endoscope with a synthetic view generated from one or more imaging modalities. The synthetic view is three-dimensional, and includes information obtained not just from the surface of an imaged organ, but also the interior portions thereof. A model used for generating the synthetic view can include the depth information of the corresponding portions, which in turn can be used in rendering, in the synthetic view, portions that are not directly visible in the live view. Presenting the synthetic view in registration with a corresponding live view can thus allow a surgeon to visualize portions of tissue/organ that are not just at the surface of the organ, but at various depths along different lines-of-sight. In some implementations, the augmented view can include the synthetic view overlaid on a corresponding live view. In other implementations, the synthetic view can be rendered without the corresponding live view, but registered with the corresponding live view. Because the synthetic view is generated based on a model that includes information about various tissues at various depths within the organ, the synthetic view can be manipulated to make portions at different depths at least partially transparent to allow for visualizing other portions in the interior of the organ. This may be referred to as cut-through-visualization, and is illustrated below in additional details. In some implementations, the synthetic view can be made interactive, allowing for the placement of virtual markers, rulers etc. on the augmented view. This can allow the surgeon, for example, to use such virtual markers in demarcating the boundary of a tumor, and/or measuring depths and dimensions of various portions of the organ, including of endophytic masses.

The model that is used to generate the synthetic view can be obtained using images of one or more modalities. The example below uses, as a primary example, the modality of CT. However, other modalities can be used, depending on, for example, the type of information that is desired to be presented to the surgeon. In some implementations, a preoperative CT-scan of the patient can be obtained in an offline process, and the obtained images can be used to generate the model used in generating the synthetic views in run time. In some implementations, the output of the CT process can include a set of raw images (e.g., a set of raw DICOM images), wherein each image is a matrix of pixels. In some implementations, the pixels can be grayscale pixels representing a radiodensity sample of the tissue measured in Hounsfield unit.

Figure 5:
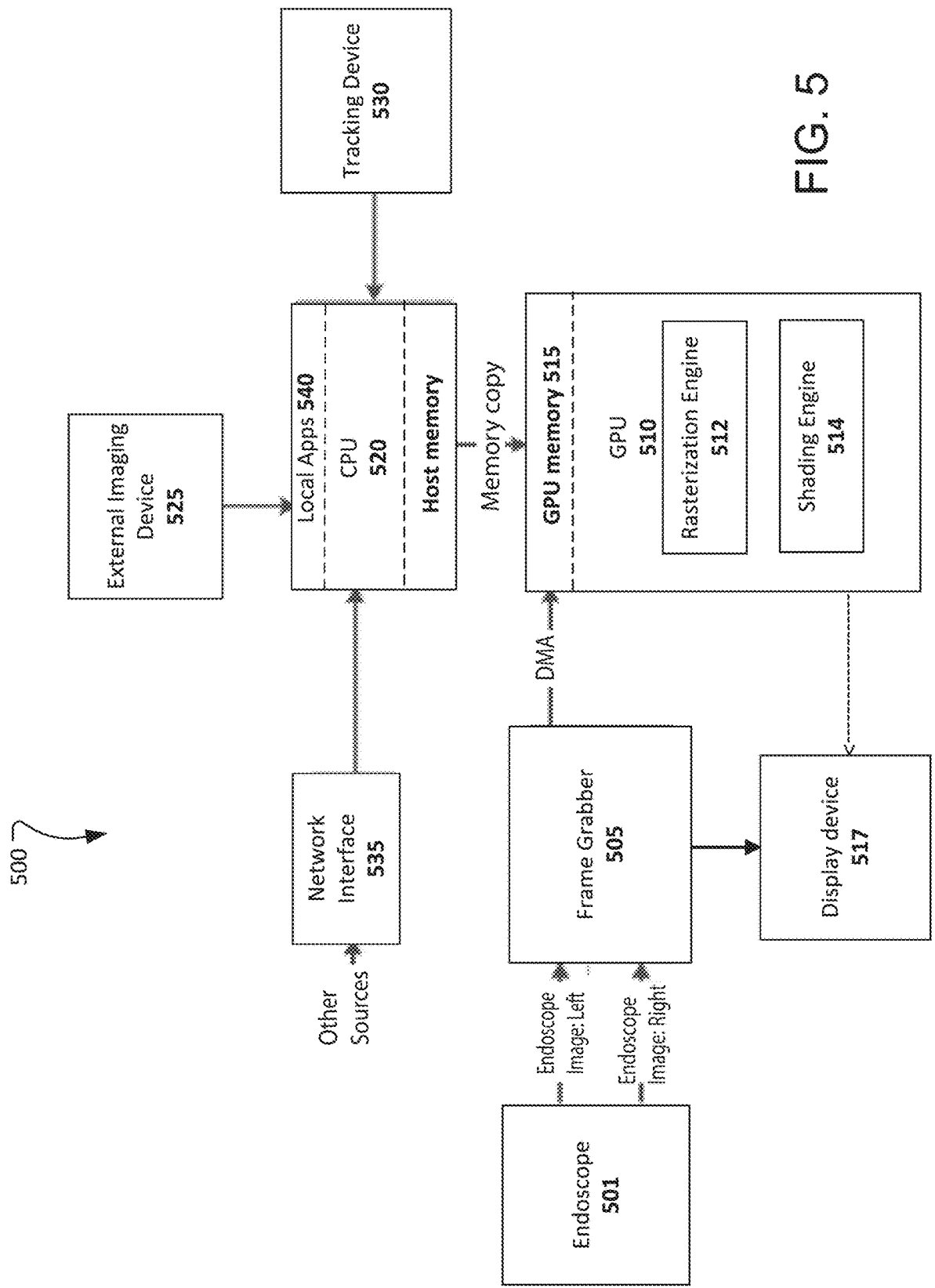
FIG. 5 is a block diagram of an example of a system usable for generating the augmented views described herein.

In some implementations, a segmentation process (using, for example, a multi-class segmentation algorithm) can be performed on the set of raw images to label all pixels that are associated with a particular anatomy. In some implementations, this can produce a new image set wherein each image includes a set of labels identifying the corresponding anatomical organs or tissues. For example, the new image set (S) can include a matrix of integer labels identifying anatomical structure e.g. parenchyma, vessels etc. A space-partitioning algorithm can then be applied to S to extract a triangle mesh (denoted as $M_L$) for each label L identified in S. This results in a one to one mapping between a label L and the mesh $M_L$ that represents it. The collection of all triangle meshes generated at this stage can be referred to as M. The triangle meshes can be represented as a set of vectors representing a model of an anatomical organ, wherein the set of vectors are produced from a representation of the organ under one or more imaging modalities The technology described herein includes a rendering process for rendering the set of triangle meshes M onto the screen to generate the synthetic view described above. In some implementations, the synthetic view can be made interactive, to allow for various interactions described herein. For example, based on the label associated with each mesh $M_L$, particular types of tissues may be displayed/highlighted in the augmented view to improve the visualization of the surgical scene for the surgeon. FIG. 5 is an example block diagram of a system 500 for generating an augmented view from images obtained from multiple sources. In some implementations, the system 500 can include a frame grabber unit 505 that digitizes incoming video frames from an endoscope 501, and transfers the digitized images to a graphics-processing unit (GPU) 510 via remote direct memory access (RDMA) to the GPU memory 515. The incoming video frames can be sent to the display device from the GPU 510, thereby avoiding the central processing unit (CPU) 620 in the processing path of the images. This in turn may keep the latency associated with the endoscopic images below a tolerable threshold. In some implementations, data from one or more other sources (e.g., an external imaging device 525 or a tracking device 530) may traverse through both the CPU 520 and the GPU 510 before being displayed on the display device. The system 500 may also include a network interface card 535 for routing data from one or more sources to the CPU 520. In some implementations, the composed images may be routed back to the frame grabber 505 via RDMA transfer and the video output to the display device 517 may be provided via the frame grabber. In some implementation, the video inputs and video outputs to/from the frame grabber 505 may be routed via a high bandwidth fiber optic link. In some implementations, the CPU 520 may execute one or more applications 540 (e.g., segmentation, rasterization, shading etc.) for processing the data received from the one or more sources.

In some implementations, the GPU 510 (or the CPU 520) includes a rasterization engine 512 that implements a rasterization process on the triangle meshes. For example, for each triangle mesh $M_L$ in M, there may exist a vertex list and a triangle list. Each entry in the vertex list can include, for example, the position, color and the anatomical label associated with that vertex. Each entry in the triangles list can include, for example, a vector of three integer-based components, where each component is an associated index to a vertex in the vertex list. These two lists can be supplied to a rasterization pipeline implemented by the rasterization engine 512. An example of a rasterization pipeline that may be used in conjunction with technology described herein is described in: Shirley P. et al., *Fundamentals of Computer Graphics*, AK Peters Ltd. (2009), $4^{th}$ Edition, Chapter 3—Triangle Rasterization, the foregoing content being incorporated by reference herein.

In some implementations, the rasterization engine 512 can be configured to generate, for each pixel position that corresponds to a live view of the organ on the display device 517, a set of fragment vectors, each of which represents a corresponding portion of the organ at various depths along a line-of-sight corresponding to the pixel. In some implementations, each fragment-vector can include a depth value of a location of the corresponding portion associated with the fragment, an identifier L representing the closest intersecting object $M_L$, and a color value associated with the corresponding portion. The depth value can represent a distance of the location from a reference point such as a point along the corresponding line-of-sight. In some implementations, the reference point corresponds to the tip of the endoscope.

In some implementations, the GPU 510 (or the CPU 520) includes a shading engine 514. The shading engine 514 can be configured to implement a custom fragment shading process that generates a color or grayscale value for a pixel based on a list of all fragments produced by the rasterization engine 512 for that pixel. For example, for each pixel coordinate position on the screen, a linked-list of all fragment vectors that are generated in the projection space for that pixel position can be stored in the memory 515 of the GPU. After the rasterization process is completed, the shading engine 514 can be configured to collect the list of fragments produced by the rasterization engine 512 for every pixel position that corresponds to a live view of the organ on the display device 517.

In some implementations, each fragment vector can include a fragment color, and the depth and the anatomical label associated with the corresponding mesh component $M_L$. In some implementations, the fragment vectors can be sorted, for example, by the depth component of the entries in the list, and the sorted list of fragment vectors can be stored in the memory 515 of the GPU 510.

The shading engine can be configured to generate a color/grayscale value for each of a set of pixels that correspond to a live view of an organ. The generation of such pixel values can be made adaptive and/or interactive, based on, for example, user-input. For example, the surgeon can select a particular class of anatomical tissue to be displayed intraoperatively, and fragment vectors corresponding to the selection can be obtained accordingly for rendering in the augmented view. In some implementations, the selection may be retained, at least for a predetermined period of time or until changed, as a current label of focus for the surgeon. In some implementations, upon receipt of the user-input for a particular set of pixels (e.g., when the surgeon taps on a screen or provides user-input using another input device), the pixel coordinate (or coordinates) of the tapped point or region can be provided to the shading engine. In response, the shading engine 514 can be configured to retrieve the list of fragment vectors, and perform a search through the list to find a suitable fragment vector (e.g., the closest fragment vector associated with the selected pixel(s)).

The shading engine 514 can also be configured to generate a pixel value for each of the corresponding pixels based on the one or more fragment vectors identified for the selection. For example, the pixel values can be generated based on the color values and depth values associated with the corresponding fragment-vectors. This can include, for example, sorting the corresponding fragment-vectors based on the associated depth values (unless they are already sorted in that order), assigning a transparency factor to each of the color values associated with the corresponding fragment vectors, and generating the pixel value as a weighted combination of the color values weighted by the corresponding transparency factors.

Figure 6B:
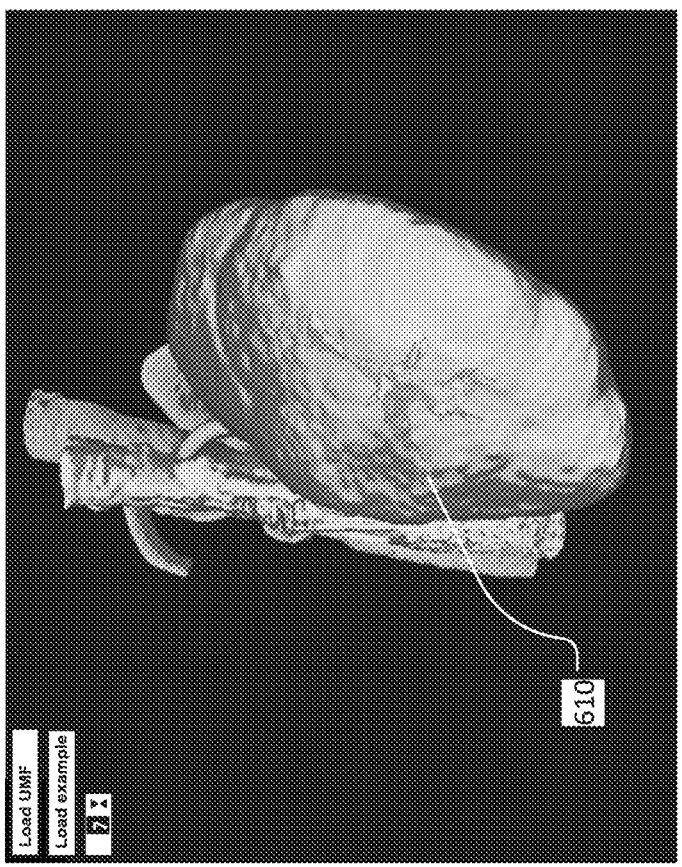
FIGS. 6A and 6B are examples of augmented views generated in accordance with technology described herein.
Figure 6A:
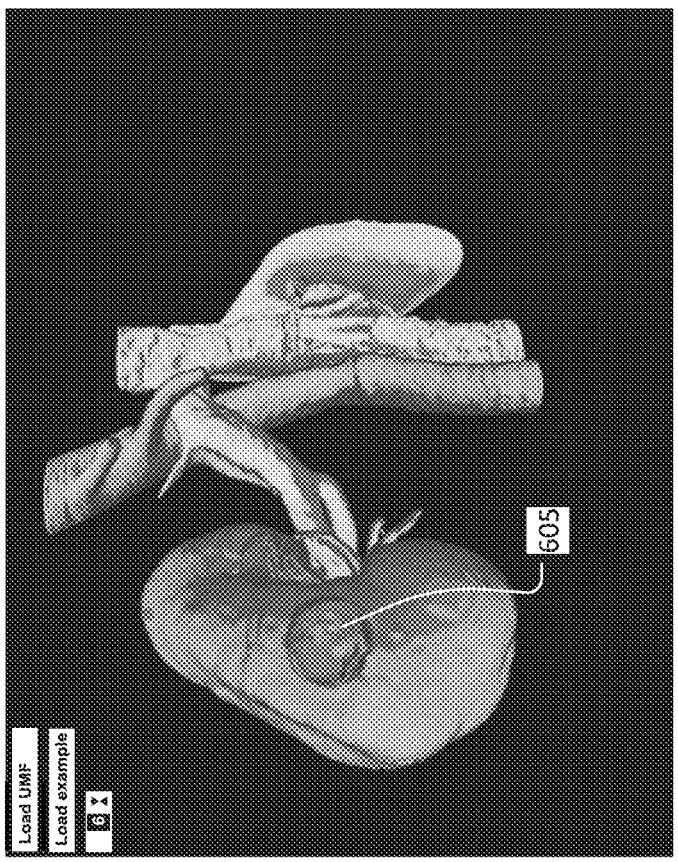

In some cases, this may allow for a visualization where fragments corresponding to one or more occluding portions of the organ are rendered as transparent (or substantially transparent) such that one or more portions or tissues that are occluded in the live view are made visible to the surgeon. Such visualization can be referred to as "cut-through visualization" that allows for presenting occluded portions such as endophytic masses or vasculature, which may not otherwise be visible to the surgeon. Examples of such augmented visualization are shown in FIGS. 6A and 6B. Specifically FIG. 6A shows the augmented view of an organ where at least a portion of endophytic mass 605 is made visible to the surgeon. Because the endophytic mass 605 represents a different tissue type (e.g., a tumor, as determined for example using imaging under a particular modality), the color values for the tissue type can be made different in order to clearly present the boundary of the tumor as compared to heathy portions of the organ. In FIG. 6B, vasculature 610 underlying the parenchyma of the organ is made visible to the surgeon. In doing so, the portions of the organ (e.g., parenchyma) occluding the vasculature is made at least partially transparent such that the underlying vasculature (or other tissues) are rendered on the display device for the surgeon.

Figure 7A:
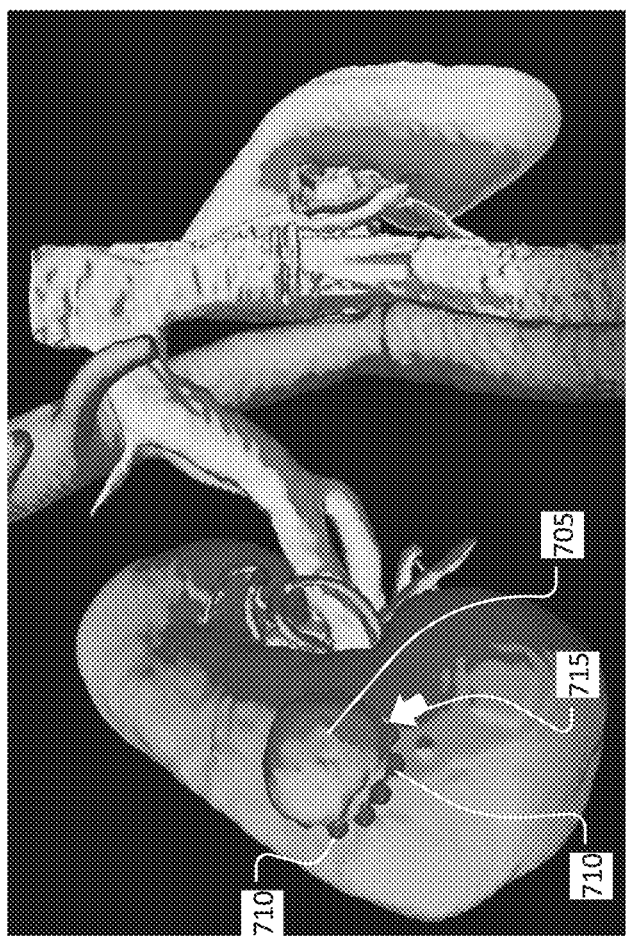
FIGS. 7A and 7B are examples of interactive augmented views usable for marking the boundary of a tumor.
Figure 7B:
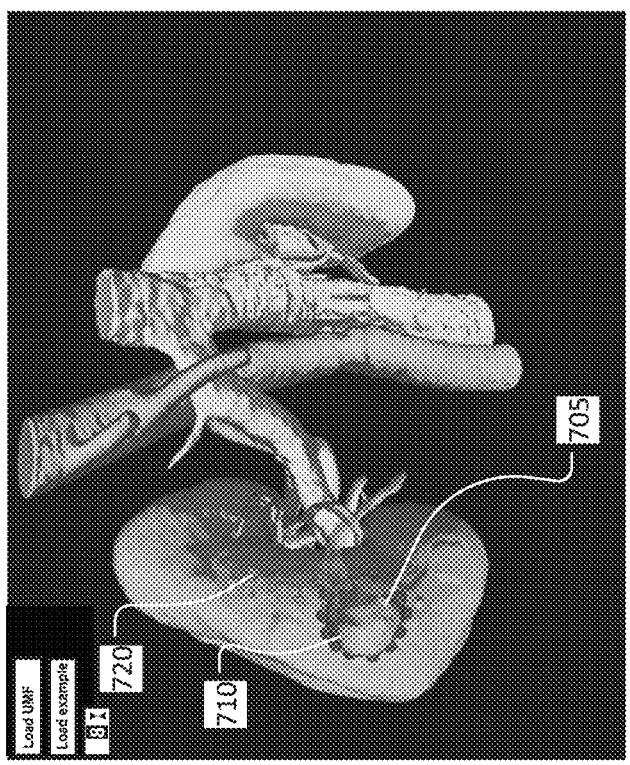

In some implementations, the augmented view generated by the technology described herein can be made interactive. An example of such interactive augmented views are shown in FIGS. 7A and 7B. Specifically, FIG. 7A shows an example where the surgeon has marked the boundary of a tumor 705 using multiple virtual markers 710. This can be done, for example, by moving a pointer 715 to a desired portion of the augmented view and clicking. Depending on a selected mode of operation, such user-input can place a virtual marker 710 on the rendered augmented view. If the live view is changed (e.g., by zooming out the endoscope cameras), the virtual markers are adaptively re-rendered in the augmented view to maintain their relative locations with respect to the corresponding physical portions of the organ. This is illustrated in FIG. 7B where the view is zoomed out with respect to that in FIG. 7A. In this example, the virtual markers 710 are readjusted such that they continue to represent the boundary of the tumor 705 in the changed view. Such ability to place adaptive virtual markers in the augmented view can help in avoiding the use of energy tools (used to burn markers directly on the tissue) or physical markers that the surgeon may have to otherwise use. This in turn can make the overall surgical process less time consuming and/or less invasive (for example by preventing the elasticity of tissue being affected by the process of burning).

Figure 8A:
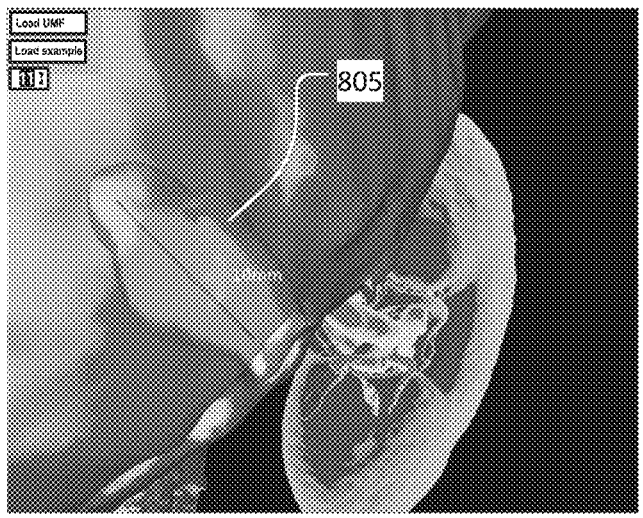
FIGS. 8A-8C show examples of augmented views with overlaid distance measurements.
Figure 8B:
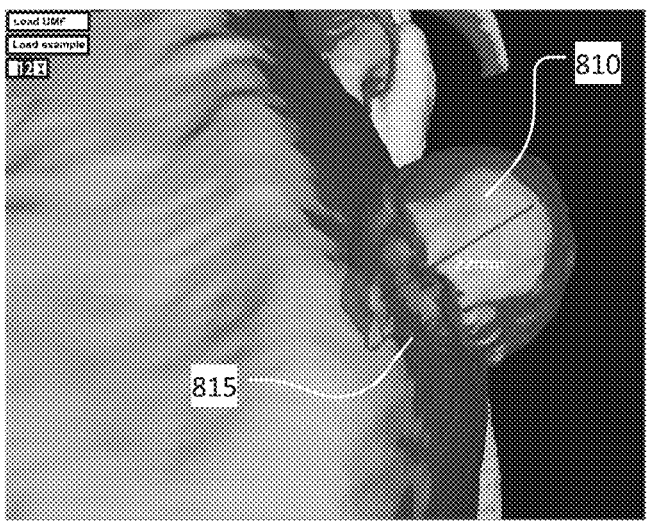
Figure 8C:
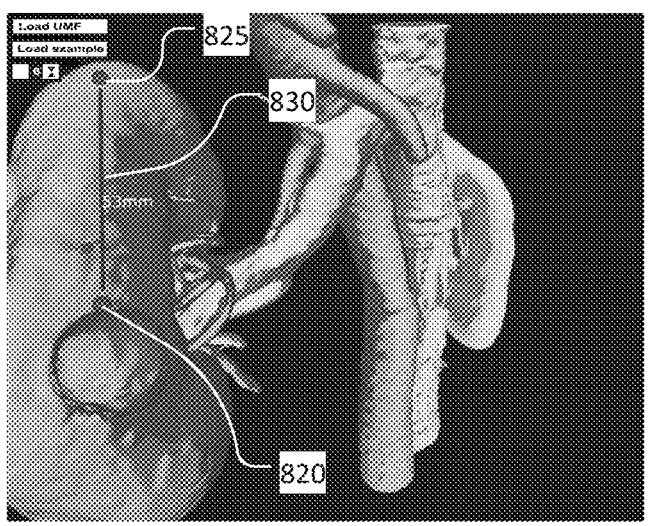

In some implementations, the technology described herein also allows for measuring portions of the surgical scene directly in the augmented view. Illustrative examples of such functionalities are shown in FIGS. 8A-8C. Specifically, FIG. 8A shows how the technology described herein allows for directly measuring the dimension of an endophytic mass 805 that would not even be visible in a regular live view. However, in the augmented view illustrated in FIG. 8A, the surgeon can simply identify the two end points of the measurement, and the corresponding distance between the two may be determined using the depth information in the corresponding fragment vectors. In some implementations, the measured distance may be displayed on augmented view and adaptively changed, for example, to represent the size of the endophytic mass as the surgeon cuts away portions of such mass. FIG. 8B shows another example where the distance is measured between a first point that is at a portion 810 of a tumor that protrudes out of an organ, and a second point that is in an endophytic portion 815 of the tumor.

In some implementations, a trajectory of a measurement ruler may also be specified in addition to its start and end points. An illustrative example is shown in FIG. 8B. In this example, apart from the start point 820 and the end point 825, the trajectory 830 of the ruler can be specified to be along the surface (e.g., parenchyma) of the organ on which the points are located. This can provide the distance along the curved surface between the two points rather than the shortest distance through the organ. The distance along the connecting surface can be computed, for example, based on the depth information corresponding to the fragment vectors for the portions along the trajectory 830.

Figure 9:
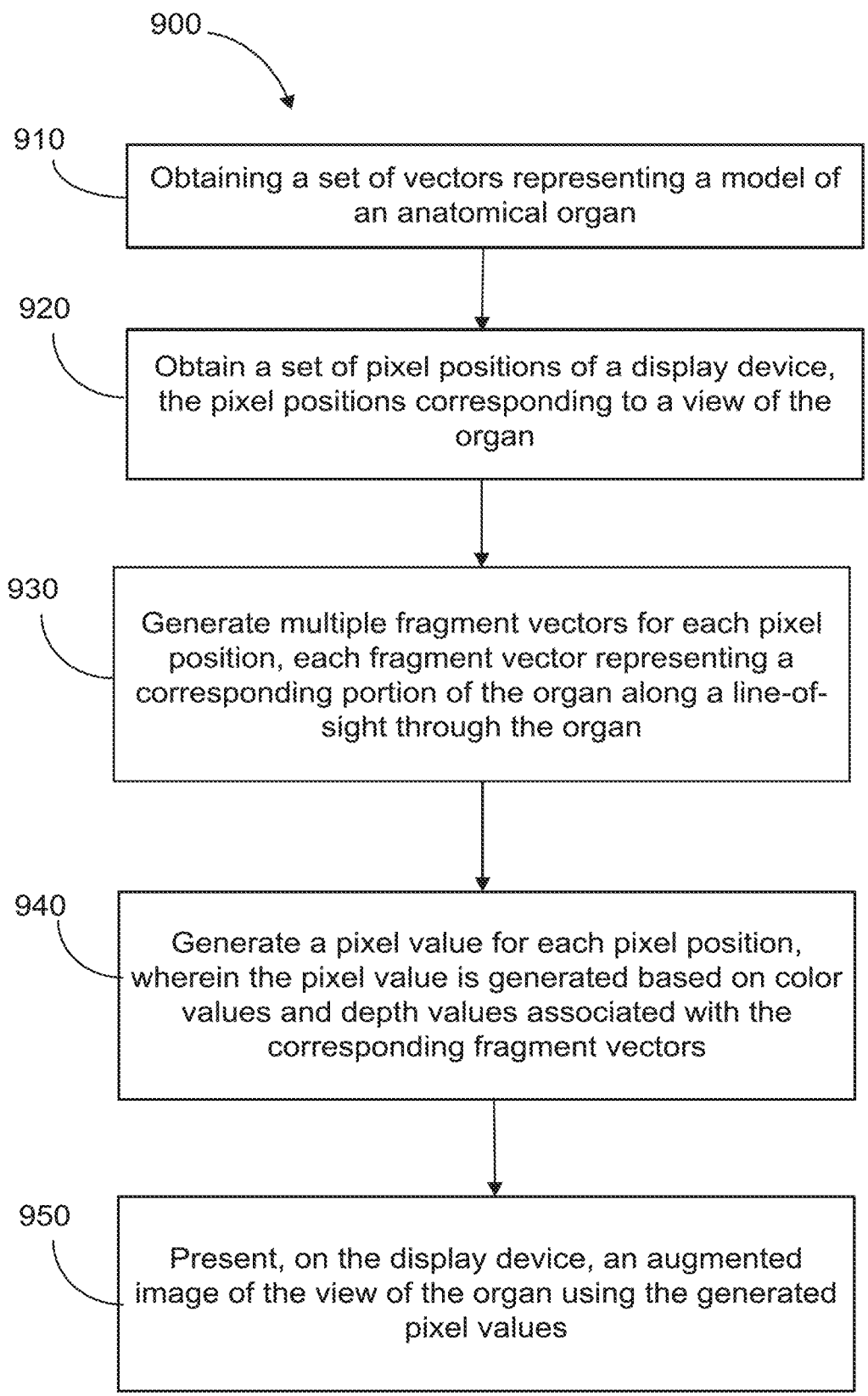
FIG. 9 is a flowchart illustrating an example process of providing visual feedback during a surgical process.

FIG. 9 is a flowchart illustrating an example process 900 for providing visual feedback during a surgical process. In some implementations, at least a portion of the process 900 can be executed in the GPU 510 described above with reference to FIG. 5. Operations of the process 900 includes obtaining a set of vectors representing a model of an anatomical organ (910). The set of vectors can be produced from a representation of the organ as imaged under one or more imaging modalities. The one or more imaging modalities can include at least one of: computerized tomography (CT), ultrasound imaging, positron emission tomography-CT (PET-CT), a single-photon emission CT (SPECT), magnetic resonance imaging (MRI), and a cone-beam CT (CBCT). In some implementations, the set of vectors can be substantially similar to the set of vectors M (or a portion thereof) as described above with reference to FIG. 5. In some implementations, the set of vectors can include multiple sub-vectors (e.g., a vector $M_L$ described above) each representing a triangle mesh representing a particular type of anatomical structure in the organ. Each of the multiple sub-vectors can include a list of vertices and triangles associated with the corresponding triangle mesh.

Operations of the process 900 also includes obtaining a set of pixel positions of a display device, the pixel positions corresponding to a view of the organ (920). The view of the organ can correspond to a live view as obtained using one or more endoscope cameras. Operations of the process further includes generating, using at least a portion of the set of vectors, multiple fragment-vectors for each pixel position in the set of pixel positions, the multiple fragment-vectors each representing a corresponding portion of the organ along a line-of-sight through the organ (930). The fragment vectors can be substantially similar to the fragment vectors described above with reference to FIG. 5. In some implementations, each fragment-vector can include a depth value of a location of the corresponding portion associated with the fragment, a color value associated with the corresponding portion, and an identifier of a different fragment vector corresponding to an adjacent portion. In some implementations, each fragment-vector can include a parameter identifying a tissue-type of the corresponding portion associated with the fragment. In some implementations, the multiple fragment vectors are generated using a rasterization process on the portion of the set of vectors Operations of the process 900 also includes generating a pixel value for each pixel position in the set of pixel positions, wherein the pixel value is generated based on the color values and depth values associated with the corresponding fragment-vectors (940). Generating the pixel value can include sorting the corresponding fragment-vectors based on the associated depth values, assigning a transparency factor to each of the color values associated with the corresponding fragment vectors, and generating the pixel value as a weighted combination of the color values weighted by the corresponding transparency factors. In some implementations, the transparency factors are assigned based on a user input indicative of a depth of visualization. In some implementations, the transparency factors are assigned based on a user input indicative of a type of tissue to be displayed on the augmented image.

Operations of the process 900 also includes presenting, on the display device, an augmented image of the view of the organ using the generated pixel values (950). The augmented image of the view can be substantially similar to the augmented views described above, including the ones illustrated in FIGS. 6a, 6B, 7A, 7B, and 8A-8C. The process 900 can further include receiving, responsive to presenting the augmented image, user input comprising one or more markers identifying particular portions on the organ, and presenting the one or more markers overlaid on the augmented image. The one or more markers can be substantially similar to the virtual markers described above with reference to FIGS. 7A and 7B. The locations of the one or more markers in the augmented image can be updated with changes to the locations of the particular portions in the view of the organ.

In some implementations, the process 900 can also include receiving, responsive to presenting the augmented image, user input identifying two discrete portions on the organ, computing, based at least on information in the fragment-vectors corresponding to the two discrete portions, a distance between the two portions, and presenting the computed distance overlaid on the augmented image. In some implementations, the distance can be presented, substantially as illustrated in the FIGS. 8A-8C. For example, the distance between the two discrete portions can be computed as a distance along a surface of the organ on which the portions are located, or the distance can be computed as a distance through the organ. In some implementations, a representation of a line connecting the two discrete portions along a surface of the organ can be overlaid on the display of the augmented image. In some implementations, at least one of the two discrete portions can represent a boundary of an endophytic mass located at a depth under the surface of the organ.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of providing visual feedback during a surgical process on a display device, the method comprising:
    obtaining a set of vectors representing a model of an anatomical organ, the set of vectors produced from a representation of the organ as imaged under one or more imaging modalities;
    obtaining a set of pixel positions of the display device, the set of pixel positions corresponding to a view of the organ;
    generating, using at least a portion of the set of vectors, multiple fragment-vectors for each pixel position in the set of pixel positions, the multiple fragment-vectors each representing a corresponding portion of the organ along a corresponding line-of-sight through the organ, each fragment-vector of the multiple fragment-vectors comprising:
        (i) a depth value of a location of the corresponding portion associated with the fragment-vector, the depth value representing a distance of the location from a reference point,
        (ii) a color value associated with the corresponding portion associated with the fragment-vector,
        (iii) a first identifier of a different fragment-vector of the multiple fragment-vectors associated with an adjacent portion, and
        (iv) a second identifier of a tissue type corresponding to the corresponding portion associated with the fragment-vector;
    generating a pixel value for each pixel position in the set of pixel positions, wherein for each pixel position in the set of pixel positions, the pixel value is generated based on the color values and depth values associated with the multiple fragment-vectors corresponding to the pixel position; and
    presenting, on the display device, an augmented image of the view of the organ using the generated pixel values.

2. The method of claim 1, wherein the one or more imaging modalities comprise at least one of: computerized tomography (CT), ultrasound imaging, positron emission tomography-CT (PET-CT), a single-photon emission CT (SPECT), magnetic resonance imaging (MM), or a cone-beam CT (CBCT).

3. The method of claim 1, wherein the set of vectors comprises multiple sub-vectors each representing a triangle mesh representing a particular type of anatomical structure in the organ.

4. The method of claim 3, wherein each of the multiple sub-vectors comprises a list of vertices and triangles associated with the corresponding triangle mesh.

5. The method of claim 1, wherein generating the pixel value for each pixel position in the set of pixel positions comprises:
sorting the multiple fragment-vectors corresponding to the pixel position based on the associated depth values;
assigning a transparency factor to each of the color values associated with the multiple fragment-vectors corresponding to the pixel position; and
generating the pixel value as a weighted combination of the color values weighted by the corresponding transparency factors.

6. The method of claim 5, wherein the transparency factors are assigned based on a user input indicative of a depth of visualization.

7. The method of claim 5, wherein the transparency factors are assigned based on a user input indicative of a type of tissue to be displayed on the augmented image.

8. The method of claim 1, further comprising:
receiving, responsive to presenting the augmented image, user input comprising one or more markers identifying particular portions on the organ; and
presenting the one or more markers overlaid on the augmented image, wherein locations of the one or more markers in the augmented image are updated with changes to locations of the particular portions in the view of the organ.

9. The method of claim 1, further comprising:
receiving, responsive to presenting the augmented image, user input identifying two discrete portions on the organ;
computing, based at least on information in the fragment-vectors corresponding to the two discrete portions, a distance between the two discrete portions; and
presenting the computed distance overlaid on the augmented image.

10. The method of claim 9, further comprising presenting, overlaid on the augmented image, a representation of a line connecting the two discrete portions along a surface of the organ on which the two discrete portions are located.

11. The method of claim 9, wherein at least one of the two discrete portions represents a boundary of an endophytic mass located at a depth under a surface of the organ.

12. The method of claim 1, wherein the multiple fragment-vectors are generated using a rasterization process on at least the portion of the set of vectors.

13. A surgical system comprising:
a display device; and
a shading engine comprising one or more processing devices, wherein the shading engine is configured to:
obtain a set of vectors representing a model of an anatomical organ, the set of vectors produced from a representation of the organ as imaged under one or more imaging modalities,
obtain a set of pixel positions of the display device, the set of pixel positions corresponding to a view of the organ,
generate, using at least a portion of the set of vectors, multiple fragment-vectors for each pixel position in the set of pixel positions, the multiple fragment-vectors each representing a corresponding portion of the organ along a corresponding line-of-sight through the organ, each fragment-vector of the multiple fragment-vectors comprising:
(i) a depth value of a location of the corresponding portion associated with the fragment-vector, the depth value representing a distance of the location from a reference point,
(ii) a color value associated with the corresponding portion associated with the fragment-vector,
(iii) a first identifier of a different fragment vector of the multiple fragment-vectors associated with an adjacent portion, and
(iv) a second identifier of a tissue type corresponding to the corresponding portion associated with the fragment-vector;
generate a pixel value for each pixel position in the set of pixel positions, wherein for each pixel position in the set of pixel positions, the pixel value is generated based on the color values and depth values associated with the multiple fragment-vectors corresponding to the pixel position, and
present, on the display device, an augmented image of the view of the organ using the generated pixel values.

14. The surgical system of claim 13, wherein the one or more imaging modalities comprise at least one of: computerized tomography (CT), ultrasound imaging, positron emission tomography-CT (PET-CT), a single-photon emission CT (SPECT), magnetic resonance imaging (MM), or a cone-beam CT (CBCT).

15. The surgical system of claim 13, wherein the set of vectors comprises multiple sub-vectors each representing a triangle mesh representing a particular type of anatomical structure in the organ.

16. The surgical system of claim 15, wherein each of the multiple sub-vectors comprises a list of vertices and triangles associated with the corresponding triangle mesh.

17. The surgical system of claim 13, wherein generating the pixel value for each pixel position in the set of pixel positions comprises:
sorting the multiple fragment-vectors corresponding to the pixel position based on the associated depth values;
assigning a transparency factor to each of the color values associated with the multiple fragment-vectors corresponding to the pixel position; and
generating the pixel value as a weighted combination of the color values weighted by the corresponding transparency factors.

18. The surgical system of claim 17, wherein the transparency factors are assigned based on a user input indicative of a depth of visualization.

19. The surgical system of claim 17, the transparency factors are assigned based on a user input indicative of a type of tissue to be displayed on the augmented image.

20. One or more machine-readable non-transitory storage devices encoded with machine-readable instructions configured to cause one or more processing devices to perform operations comprising:

obtaining a set of vectors representing a model of an anatomical organ, the set of vectors produced from a representation of the organ as imaged under one or more imaging modalities;

obtaining a set of pixel positions of a display device, the set of pixel positions corresponding to a view of the organ;

generating, using at least a portion of the set of vectors, multiple fragment-vectors for each pixel position in the set of pixel positions, the multiple fragment-vectors each representing a corresponding portion of the organ along a line-of-sight through the organ, each fragment-vector of the multiple fragment-vectors comprising:

(i) a depth value of a location of the corresponding portion associated with the fragment-vector, the depth value representing a distance of the location from a reference point, (ii) a color value associated with the corresponding portion associated with the fragment-vector, (iii) a first identifier of a different fragment vector of the multiple fragment-vectors associated with an adjacent portion, and (iv) a second identifier of a tissue type corresponding to the portion associated with the fragment-vector;

generating a pixel value for each pixel position in the set of pixel positions, wherein for each pixel position in the set of pixel positions, the pixel value is generated based on the color values and depth values associated with the multiple fragment-vectors corresponding to the pixel position; and presenting, on the display device, an augmented image of the view of the organ using the generated pixel values.

* * * * *

UNITED STATES PATENT AND TRADEMARK OFFICE
CERTIFICATE OF CORRECTION

PATENT NO. : 11,393,178 B2
APPLICATION NO. : 17/266304
DATED : July 19, 2022
INVENTOR(S) : Pourya Shirazian, Mahdi Azizian and Daniel Proksch It is certified that error appears in the above-identified patent and that said Letters Patent is hereby corrected as shown below:

In the Claims

In Column 15, Line 5, Claim 2, please replace "(MM)," with -- (MRI), --.

In Column 16, Line 38, Claim 14, please replace "(MM)," with -- (MRI), --.

In Column 17, Line 24, Claim 20, please replace "portion" with -- corresponding portion --.

Signed and Sealed this
Sixth Day of September, 2022

Katherine Kelly Vidal
*Director of the United States Patent and Trademark Office*